United States Patent [19]

Yamazaki et al.

[11] 3,994,960

[45] Nov. 30, 1976

[54] PROCESS FOR PREPARING DIALKYL OXALATES

[75] Inventors: Toshiharu Yamazaki; Masao Eguchi; Shinicharo Uchiumi; Akira Iwayama; Mitsuo Takahashi; Masaru Kurahashi, all of Ube, Japan

[73] Assignee: UBE Industries, Ltd., Ube, Japan

[22] Filed: Mar. 21, 1975

[21] Appl. No.: 560,829

[30] Foreign Application Priority Data
Apr. 5, 1974 Japan.............................. 49-38010
June 26, 1974 Japan.............................. 49-72251

[52] U.S. Cl. ........................... 260/485 R; 260/463; 260/488 K
[51] Int. Cl.² ....................................... C07G 69/36
[58] Field of Search ........................... 260/485 R, 82

[56] References Cited
FOREIGN PATENTS OR APPLICATIONS
2,213,435  10/1973  Germany ...................... 260/485 R OTHER PUBLICATIONS
Fenton et al., J. Org. Chem. 39, No. 5, pp. 701–704, (1974).

Primary Examiner—Jane S. Myers
Attorney, Agent, or Firm—Flynn & Frishauf

[57] ABSTRACT

A process for preparing dialkyl oxalates by reacting an aliphatic alcohol with carbon monoxide and oxygen under pressure. In the present process, (a) a catalyst consisting of a mixture of a salt of a platinum group metal and a salt of copper or iron and (b) an accelerator composed of one or more compounds selected from the group consisting of carbonates, hydrogen carbonates, nitrates, sulfates, hydroxides and carboxylates of an alkali metal and of an alkaline earth metal, pyridine, quinoline, glycine, alanine, urea, thiourea, formamide, acetamide, acetylacetone, ethyl acetoacetate, dimethylglyoxime, a tertiary amine, and a substituted or unsubstituted triphenyl phosphine are both used.

15 Claims, No Drawings

PROCESS FOR PREPARING DIALKYL OXALATES

This invention relates to a process for preparing dialkyl oxalates. More particularly, this invention relates to an improvement in a process for preparing a dialkyl oxalate by the reaction of an aliphatic alcohol with carbon monoxide and oxygen.

Dialkyl oxalates have various industrial utilities, for instance, as reagents for analysis, solvents, and starting materials for oxamide, orotic acid, etc.

In general, dialkyl oxalates have been heretofore prepared by heating oxalic anhydride with an aliphatic alcohol in the presence of conc. sulfuric acid. On the other hand, U.S. Pat. No. 3,391,136 of Donald M. Fenton et al. discloses a process for preparing dialkyl oxalates (hereinafter referred to as "prior process") wherein an aliphatic alcohol is contacted with CO and $O_2$ under pressure in the presence of a catalyst composed of a mixture of a salt of a platinum group metal and a salt of copper or iron. However, said prior process is performed under anhydrous conditions, preferably, by employing an alkyl orthoformic ester as a dehydrating agent, since the production of a dialkyl oxalate is prevented by water formed in situ according to the reactions taking place.

The principal reaction is supposed as follows:

$$2CO + 2ROH + \frac{1}{2}O_2 \rightarrow (COOR)_2 + H_2O \quad (1)$$

The side reactions are supposed as follows $$CO + 2ROH + \frac{1}{2}O_2 \rightarrow CO(OR)_2 + H_2O \quad (2)$$

$$2ROH + O_2 \rightarrow R'COOR + 2H_2O \ [R = R'CH_2-] \quad (3)$$

$$3ROH + \frac{1}{2}O_2 \rightarrow R'CH(OR)_2 + 2H_2O \quad (4)$$

$$2ROH \rightarrow ROR + H_2O \quad (5)$$

We have followed up this fact by our experiments and confirmed that a dialkyl oxalate is in no way formed unless a dehydrating agent is employed. Moreover, according to our experiments, it is required in the prior process that the reaction should be conducted under completely anhydrous conditions by the use of a dehydrating agent, since the yield of a dialkyl oxalate is extremely lowered due to the presence of even a minor amount of water in the reaction system, and thus very difficult and complicated procedures and control are required. Moreover, a dehydrating agent, particularly an alkyl orthoformic ester, is not only highly expensive but also convertible to an entirely different compound after the dehydration reaction so that this converted compound is incapable of being practically reused as a dehydrating agent. Therefore, a production cost of dialkyl oxalates becomes highly expensive in the prior process. Further, in the prior process, the selectivity of a dialkyl oxalate seems to be very low due to the by-production of a large amount of carbonic diesters, fatty acid esters and the like, which is believed to be caused by the presence of a large amount of a dehydrating agent. Accordingly, the prior process seems to be commercially unsatisfactory.

We have conducted research in order to improve the prior process and to find a commercially advantageous process for preparing dialkyl oxalates. More specifically, experiments have been made for the purpose of finding a reaction accelerator having the following characteristic: A dialkyl oxalate can be economically produced, even in the presence of water in the reaction system, by the addition of a minor amount of the reaction accelerator into the system instead of a large amount of a dehydrating agent.

As a result of our research, it has been found that a dialkyl oxalate can be produced in a high yield and a high selectivity, even in the presence of water, by reacting an aliphatic alcohol with CO and $O_2$ under pressure in the presence of a. a catalyst consisting of a mixture of a salt of a platinum group metal and a salt of copper or iron, and b. an accelerator composed of one or more compounds selected from the group consisting of carbonates, hydrogen carbonates, nitrates, sulfates, hydroxides and carboxylates of an alkali metal and of an alkaline earth metal, pyridine, quinoline, glycine, alanine, urea, thiourea, formamide, acetamide, acetylacetone, ethyl acetoacetate, dimethylglyoxime, a tertiary amine, and a substituted or unsubstituted triphenyl phosphine and this invention has been completed upon this discovery.

In contrast, chlorides and bromides of an alkali metal or of an alkaline earth metal such as potassium chloride, magnesium bromide and lithium chloride are not effective as the reaction accelerator.

According to the present invention, there is no need for an expensive dehydrating agent to maintain the reaction system under anhydrous conditions nor for complicated procedures as required in the prior process, by the use of a minor amount of a reaction accelerator in the reaction system, and also a dialkyl oxalate can be produced at an extremely lower production cost in comparison with the prior process. Moreover, a lesser amount of by-products such as carbonic diesters, fatty acid esters and the like is formed as compared with the prior process, and better yield and selectivity of a dialkyl oxalate can be attained.

As the aliphatic alcohol which may be employed in this invention an alcohol having from 1 to 6 carbon atoms is preferred.

Of the carbonates, hydrogen carbonates, nitrates, sulfates or hydroxides of an alkali metal or alkaline earth metal which may be used as a reaction accelerator in this invention, $K_2CO_3$, $Na_2CO_3$, $NaHCO_3$ and $NaOH$ are particularly effective, and $NaNO_3$, $Na_2SO_4$, $MgSO_4$, $CaCO_3$, $BaCO_3$, $KHCO_3$, $KNO_3$, $Ca(NO_3)_2$, $K_2SO_4$, $KOH$, $Mg(OH)_2$ and a mixture thereof may be also utilized. Further, trimethylamine, triethylamine, tripropylamine, tributylamine and the like are effective as the tertiary amine, and triphenyl phosphine and those phosphines having a halogen atom, a lower alkyl group such as methyl and ethyl, nitro group, amino group, etc., a substituents in the phenyl group are effective as the triphenyl phosphine. Effective alkali metals or alkaline earth metals of carboxylic acids are Li, K, Na, Ca, Mg, Ba and the like salts of carboxylic acids having from 1 – 6 carbon atoms such as acetic acid, propionic acid, butyric acid, valeric acid, etc.

The amount of such reaction accelerator to be added may somewhat vary upon the kind of the reaction accelerator, but it is desirable in view of the yield and selectivity of a dialkyl oxalate to employ the accelerator in an amount of 0.01 – 5 moles, preferably 0.05 – 2.5 moles, based on one mole of the catalyst.

In case the above-identified inorganic compounds are employed as the accelerator, they are advantageously used in a very minor amount of 0.5 – 2.5 moles based on one mole of the catalyst.

In case the above-identified organic compounds are employed as the accelerator, they are advantageously used in an amount of 0.5 – 30 moles, preferably 1.0 – 20 moles, based on one mole of the platinum group metal salt.

As the salt of platinum group metal and the salt of copper or iron, which are employed as a catalyst in the present invention, may be mentioned hydrochlorides, nitrates, sulfates, phosphates, acetates and the like of Pd, Pt, Rh, Ru, Ir and Cu, Fe, and such copper or iron salt is desirably used in admixture with 1 – 20 parts by weight, preferably 3 – 15 parts by weight, per 1 part by weight of the platinum group metal salt. The amount of the catalyst having the above formula to be used is 0.01 – 1.0 g., preferably 0.05 – 0.5 g., of the platinum group metal salt per 100 ml. of the aliphatic alcohol which is employed as a starting material.

In this invention, it is desirable to charge CO into a reaction vessel so that the CO pressure is 40 – 120 Kg./cm$^2$G (G means gauge pressure), since the reaction rate is slower and the yield and selectivity of dialkyl oxalate are lowered at a pressure less than 40 Kg./cm$^2$G, while the yield and selectivity of a dialkyl oxalate remain approximately constant even at a pressure of more than 120 Kg./cm$^2$G. The O$_2$ pressure usually is not more than 20 Kg./cm$^2$G so that the composition of the gas within a reaction vessel may be out of an explosive range and it is preferable for ensuring safety to charge 2 or 3 divided portions of O$_2$ into the vessel.

The reaction temperature and time period are preferably such that the reaction is effected for 1 – 5 hours after the final introduction of O$_2$ at 40° – 150° C, more preferably 60° – 120° C. After completion of the reaction, a dialkyl oxalate may be obtained by conventional procedures such as cooling, recovery of the catalyst and reaction accelerator or distillation.

This invention is more concretely explained by way of the following examples and comparative examples.

In each example, the product after completion of the reaction was quantitatively analyzed by a gas chromatography and the results are summarized in Tables 3 and 7.

EXAMPLE 1

100 ml. of methanol was charged into an autoclave. Then, a mixture of 0.1 g. of PdCl$_2$ with 1.0 g. of CuCl$_2$ and 0.81 g. of triethylamine were added thereto and CO was charged into the autoclave so as to be under a pressure of 45 Kg./cm$^2$G. The content of the autoclave was heated to 80° C. and then 5 Kg./cm$^2$G of O$_2$ was charged thereinto. The reaction was carried out at 80° C. with stirring for 2 hours.

EXAMPLES 2 – 7

Each experiment was run in the same manner as in Example 1 except that 100 ml. of methanol was used as the aliphatic alcohol, a mixture of PdCl$_2$ with CuCl$_2$ was used as a catalyst and the amount of the catalyst added, the kind and added amount of the reaction accelerator, the pressures of CO and of O$_2$ and the reaction temperature and period were as shown in Table 1.

Table 1

| | Catalyst composition (g) | | Reaction accelerator | | Pressure (Kg./cm$^2$G) | | Reaction | |
|---|---|---|---|---|---|---|---|---|
| Ex. | PdCl$_2$ | CuCl$_2$ | Compound | Added amount (g) | CO | O$_2$ | Temp. (° C) | Period (hr) |
| 2 | 0.1 | 1.0 | HCONH$_2$ | 0.36 | 45 | 5 | 80 | 2 |
| 3 | 0.1 | 1.0 | P-(C$_6$H$_5$)$_3$ | 0.16 | 50 | 5 | 80 | 2 |
| 4 | 0.1 | 0.5 | CH$_3$C=NOH<br>\|<br>CH$_3$C=NOH | 0.07 | 50 | 9 | 120 | 2 |
| 5 | 0.1 | 0.5 | CS(NH$_2$)$_2$ | 0.045 | 50 | 9 | 120 | 2 |
| 6 | 0.2 | 0.5 | CO(NH$_2$)$_2$ | 0.052 | 60 | 12 | 100 | 3 |
| 7 | 0.1 | 0.5 | H$_2$N.CH$_2$COOH | 0.046 | 50 | 9 | 100 | 2 |

EXAMPLES 8 – 15

Each experiment was run in the same manner as in Example 1 except that 100 ml. each of ethanol (Examples 8 – 10), methanol (Example 11), n-propylalcohol (Examples 12 – 13), n-butylalcohol (Example 14) and n-amylalcohol (Example 15) was used, the kind and added amount of the catalyst, the kind and added amount of the reaction accelerator, the pressures of CO and O$_2$, and the reaction temperature and period were as shown in Table 2.

Table 2

| | Platinum group metal salt | | Copper or iron salt | | Reaction accelerator | | Pressure (Kg./cm$^2$G) | | Reaction | |
|---|---|---|---|---|---|---|---|---|---|---|
| Ex. | Compound | Added amount (g) | Compound | Added amount (g) | Compound | Added amount (g) | CO | O$^2$ | Temp. (° C) | Period (hr) |
| 8 | PdCl$_2$ | 0.2 | CuCl$_2$ | 2.0 | CH$_3$COONa | 2.80 | 60 | 8 | 120 | 2 |
| 9 | PdCl$_2$ | 0.3 | CuSO$_4$ | 1.5 | (C$_2$H$_5$)$_3$N | 0.85 | 50 | 15 | 70 | 4 |
| 10 | PtCl$_2$ | 0.3 | Fe(NO$_3$)$_3$ | 2.0 | P-(C$_6$H$_4$-Cl)$_3$ | 0.62 | 50 | 8 | 70 | 4 |

Table 2-continued

| Ex. | Platinum group metal salt Compound | Added amount (g) | Copper or iron salt Compound | Added amount (g) | Reaction accelerator Compound | Added amount (g) | Pressure (Kg./cm²G) CO | O² | Reaction Temp. (° C) | Period (hr) |
| --- | --- | --- | --- | --- | --- | --- | --- | --- | --- | --- |
| 11 | RhCl₃ | 0.4 | CuCl₂ | 4.0 | 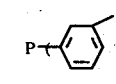 | 2.51 | 60 | 8 | 80 | 3 |
| 12 | Pd(NO₃)₂ | 0.4 | FeCl₃ | 5.0 | 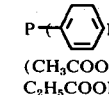 | 3.06 | 60 | 10 | 100 | 3 |
| 13 | PtCl₂ | 0.5 | FePO₄ | 4.5 | (CH₃COO)₂Ca | 1.02 | 80 | 10 | 100 | 1.5 |
| 14 | PtCl₂ | 0.1 | FeCl₃ | 2.0 | C₂H₅COOK | 0.15 | 100 | 5 | 80 | 2.5 |
| 15 | Ru₂(SO₄)₃ | 0.2 | CuCl₂ | 1.0 | C₃H₇COONa | 0.18 | 80 | 5 | 60 | 3 |

Kg./cm²G and the reaction was carried out with stirring at 120° C. for 4 hours.

Table 3

| | | Yield (m mol) *1 | | | |
| --- | --- | --- | --- | --- | --- |
| Ex. | Dialkyl oxalate | | Carbonic acid diester | | Aliphatic acid ester |
| 1 | | 23.4 | | 12.8 | 4.3 |
| 2 | | 7.5 | | 8.0 | 9.1 |
| 3 | | 6.0 | | 4.5 | 0 |
| 4 | | 7.1 | | 6.4 | 3.2 |
| 5 | dimethyl oxalate | 13.0 | dimethyl carbonate | 9.2 | methyl formate 4.4 |
| 6 | " | 12.7 | | 8.8 | 4.1 |
| 7 | | 7.1 | | 4.8 | 8.3 |
| 8 | | 22.0 | | 28.5 | 6.2 |
| 9 | diethyl oxalate | 10.2 | diethyl carbonate | 8.7 | ethyl acetate 3.3 |
| 10 | | 7.5 | | 6.6 | 2.8 |
| 11 | dimethyl oxalate | 7.7 | dimethyl carbonate | 6.0 | methyl formate 3.5 |
| 12 | di-n-propyl oxalate | 6.3 | di-n-propyl carbonate | 5.8 | n-propyl propionate 4.2 |
| 13 | " | 8.7 | " | 3.2 | " 0.7 |
| 14 | di-n-butyl oxalate | 11.8 | di-n-butyl carbonate | 8.3 | n-butyl butyrate 3.5 |
| 15 | di-n-amyl oxalate | 6.2 | di-n-amyl carbonate | 2.0 | n-amyl valerate 0.8 |
| Comparative Ex. 1 | dimethyl oxalate | 0 | dimethyl carbonate | 0 | methyl formate 6.2 |
| Comparative Ex. 2 | " | 31 | " | 2.9 | " 130 |
| Comparative Ex. 3 | diethyl oxalate | 0 | diethyl carbonate | 0 | ethyl acetate 0 |

*1: Other by-products were hardly produced in all Examples and Comparative Examples 2 and 3, but 7.6 m moles of methylal was by-produced in Comparative Example 1.

Comparative example 1

The experiment was run in the same manner as in Example 1 except that 0.26 g. of methylamine was used instead of the triethylamine.

Comparative example 2

50 ml. methanol was charged into an autoclave and a mixture of 0.1 g. of PdCl₂ with 0.5 g. of CuCl₂ and 50 ml. of methyl orthoformate were added thereto. Then, CO was charged into the autoclave so as to be under a pressure of 50 Kg./cm²G and the content thereof was heated to 120° C. After 9 Kg./cm²G of O₂ was charged into the autoclave, the reaction was carried out with stirring at 120° C. for 2 hours.

Comparative example 3

100 ml. of ethanol was charged into an autoclave and a mixture of 0.2 g. of PdCl₂ with 2.0 g. of CuCl₂ was added thereto. Then, CO was charged into the autoclave so as to be under a pressure of 60 Kg./cm²G and the content thereof was heated to 120° C. Then, O₂ was charged thereinto so as to be under a pressure of 5

EXAMPLE 16

100 ml. of methanol was charged into an autoclave. Then, a mixture of 0.1 g. of PdCl₂ with 0.5 g. of CuCl₂ and 0.59 g. of K₂CO₃ were added thereto and CO was charged into the autoclave so as to be under a pressure of 77 Kg./cm²G. The content of the autoclave was heated to 80° C. and then 10 Kg./cm²G of O₂ was charged thereinto in two divided portions. The reaction was carried out at 80° C. with stirring for 2 hours.

EXAMPLES 17 – 25

Each experiment was run in the same manner as in Example 16 except that 100 ml. of methanol was used as an aliphatic alcohol, a mixture of PdCl₂ with CuCl₂ was used as the catalyst and the amount of the catalyst added, the kind and added amount of the reaction accelerator, the pressures of CO and of O₂, and the reaction temperature and period were as shown in Table 4.

Table 4

| Example | Catalyst composition (g) PdCl$_2$ | CuCl$_2$ | Reaction/accelerator Compound | Added amount (g) | Pressure (Kg./cm$^2$G) CO | O$_2$ | Reaction Temp. (° C) | Period (hr) |
| --- | --- | --- | --- | --- | --- | --- | --- | --- |
| 17 | 0.2 | 2.0 | K$_2$CO$_3$ | 2.22 | 80 | 8 | 80 | 2.5 |
| 18 | 0.2 | 2.0 | K$_2$CO$_3$ | 1.11 | 80 | 8 | 80 | 2.5 |
| 19 | 0.1 | 1.0 | NaHCO$_3$ | 0.67 | 45 | 5 | 80 | 2 |
| 20 | 0.1 | 1.0 | NaNO$_3$ | 0.68 | 45 | 5 | 80 | 2 |
| 21 | 0.1 | 0.5 | Na$_2$SO$_4$ | 0.71 | 45 | 5 | 90 | 4 |
| 22 | 0.1 | 0.5 | Na$_2$SO$_4$ | 1.42 | 45 | 5 | 110 | 3 |
| 23 | 0.1 | 0.5 | MgSO$_4$ | 1.01 | 45 | 5 | 120 | 4 |
| 24 | 0.1 | 0.5 | MgSO$_4$ | 0.50 | 60 | 10 | 80 | 3 |
| 25 | 0.1 | 0.5 | NaOH | 0.20 | 45 | 5 | 90 | 4 |

EXAMPLES 26 – 30

Each experiment was run in the same manner as in Example 16 except that 100 ml. of ethanol was used as an aliphatic alcohol, 0.2 g. of PdCl$_2$ and 2.0 g. of CuCl$_2$ were used as the catalyst and the amount of the catalyst added, the kind and added amount of the reaction accelerator, the pressures of CO and of O$_2$, and the reaction temperature and period were as shown in Table 5.

Table 5

| Example | Reaction accelerator Compound | Added amount (g) | Pressure (Kg./cm$^2$G) CO | O$_2$ | Reaction Temp. (° C) | Period (hr) |
| --- | --- | --- | --- | --- | --- | --- |
| 26 | K$_2$CO$_3$ | 2.22 | 100 | 10 | 80 | 2 |
| 27 | K$_2$CO$_3$ | 2.22 | 55 | 8 | 100 | 1.5 |
| 28 | K$_2$CO$_3$ | 4.44 | 55 | 8 | 100 | 1.5 |
| 29 | Na$_2$CO$_3$ | 3.42 | 50 | 8 | 120 | 3 |
| 30 | Na$_2$CO$_3$ | 4.27 | 60 | 8 | 120 | 3 |

EXAMPLES 31 – 34

Each experiment was run in the same manner as in Example 16 except that 100 ml. each of n-propyl alcohol (Example 31), n-butyl alcohol (Example 32), n-amyl alcohol (Example 33) and n-hexyl alcohol (Example 34) was used as the aliphatic alcohol instead of methanol.

EXAMPLES 35 – 45

Each experiment was run in the same manner as in Example 16 except that 100 ml. each of methanol (Examples 35 – 38), ethanol (Examples 39 – 41), n-propyl alcohol (Examples 42 – 44), and n-amyl alcohol (Example 45) was used as the aliphatic alcohol and the kind and added amount of the catalyst, and the kind and added amount of the reaction accelerator were as shown in Table 6.

Table 6

| Ex. | Catalyst Platinum group metal salt Compound | Added amount (g) | Copper or iron salt Compound | Added amount (g) | Reaction accelerator Compound | Added amount (g) |
| --- | --- | --- | --- | --- | --- | --- |
| 35 | PdCl$_2$ | 0.05 | FeCl$_3$ | 0.7 | K$_2$CO$_3$ | 0.59 |
| 36 | PtCl$_2$ | 0.05 | FeCl$_3$ | 0.7 | K$_2$CO$_3$ | 0.59 |
| 37 | PtCl$_2$ | 0.1 | Fe(NO$_3$)$_3$ | 0.3 | K$_2$CO$_3$ | 0.20 |
| 38 | RhCl$_3$ | 0.1 | CuCl$_2$ | 0.3 | NaHCO$_3$ | 0.28 |
| 39 | IrCl$_3$ | 0.1 | CuCl$_2$ | 0.3 | NaHCO$_3$ | 0.28 |
| 40 | Pd(NO$_3$)$_2$ | 0.2 | FeCl$_3$ | 0.6 | Na$_2$CO$_3$ | 0.50 |
| 41 | RuCl$_3$ | 0.3 | Cu(NO$_3$)$_2$ | 1.0 | Na$_2$CO$_3$ | 0.65 |
| 42 | Ru(NO$_3$)$_3$ | 0.1 | FeCl$_3$ | 2.0 | NaOH | 0.74 |
| 43 | PdSO$_4$ | 0.5 | Fe$_2$(SO$_4$)$_3$ | 5.0 | NaOH | 1.33 |
| 44 | Rh$_2$(SO$_4$)$_3$ | 0.5 | FePO$_4$ | 5.0 | NaNO$_3$ | 2.81 |
| 45 | PdCl$_2$ | 0.1 | CuSO$_4$ | 1.2 | Na$_2$SO$_4$ | 1.00 |

Comparative example 4

100 ml. of methanol was charged into an autoclave and a mixture of 0.3 g. of PdCl$_2$ with 2.0 g. of CuCl$_2$ and then 0.36 g. of LiCl were added thereto. Thereafter, CO was charged into the autoclave so as to be under a pressure of 100 Kg./cm$^2$G and the contents thereof were heated to 60° C. Then, O$_2$ was charged in two divided portions under a pressure of 20 Kg./cm$^2$G, and the reaction was carried out at 60° C. with stirring for 3.5 hours.

Comparative example 5

The experiment was run in the same manner as in Example 17 except that 1.21 g. of KCl was used instead of the K$_2$CO$_3$.

Table 7

| Ex. | Dialkyl oxalate | Yield (m mol) *1 | Carbonic acid diester | | Aliphatic acid ester | |
|---|---|---|---|---|---|---|
| 16 | | 78.2 | | 7.2 | | 3.6 |
| 17 | | 75.0 | | 10.1 | | 0 |
| 18 | | 78.2 | | 15.3 | | 0 |
| 19 | Dimethyl | 48.1 | Dimethyl | 12.5 | Methyl | 0.9 |
| 20 | oxalate | 30.2 | carbonate | 3.1 | formate | 0 |
| 21 | | 38.0 | | 8.0 | | 2.1 |
| 22 | | 35.4 | | 10.5 | | 0.8 |
| 23 | | 10.5 | | 3.2 | | 0.7 |
| 24 | | 9.8 | | 2.1 | | 0 |
| 25 | | 42.6 | | 11.8 | | 3.7 |
| 26 | Diethyl | 69.7 | Diethyl | 7.2 | Ethyl | 1.6 |
| 27 | oxalate | 49.8 | carbonate | 9.2 | acetate | 2.0 |
| 28 | | 54.4 | | 11.3 | | 0 |
| 29 | | 62.0 | | 15.5 | | 0 |
| 30 | | 72.5 | | 16.1 | | 0 |
| 31 | Di-n-propyl oxalate | 78.8 | Di-n-propyl carbonate | 11.2 | n-Propyl propionate | 2.4 |
| 32 | Di-n-butyl oxalate | 77.5 | Di-n-butyl carbonate | 10.8 | n-Butyl butyrate | 1.2 |
| 33 | Di-n-amyl oxalate | 68.4 | Di-n-Amyl carbonate | 12.1 | n-Amyl valerate | 5.0 |
| 34 | Di-n-hexyl oxalate | 48.7 | Di-n-hexyl carbonate | 4.5 | n-Hexyl capronate | 4.2 |
| 35 | | 76.4 | | 8.5 | | 0 |
| 36 | Dimethyl oxalate | 70.5 | Dimethyl carbonate | 10.2 | Methyl formate | 0 |
| 37 | | 35.5 | | 6.2 | | 0.8 |
| 38 | | 67.0 | | 8.8 | | 0.7 |
| 39 | | 65.9 | | 7.6 | | 0.8 |
| 40 | Diethyl oxalate | 29.5 | Diethyl carbonate | 3.1 | Ethyl acetate | 1.2 |
| 41 | | 18.1 | | 3.0 | | 0.9 |
| 42 | | 11.6 | | 2.1 | | 0 |
| 43 | Di-n-propyl oxalate | 12.2 | Di-n-propyl carbonate | 2.8 | n-Propyl propionate | 0 |
| 44 | | 9.8 | | 3.3 | | 3.8 |
| 45 | Di-n-amyl oxalate | 30.8 | Di-n-Amyl carbonate | 5.4 | n-Amyl valerate | 3.0 |
| Comparative Ex. 4 | Dimethyl oxalate | 1.9 | Dimethyl carbonate | 3.0 | Methyl formate | 10.0 |
| Comparative Ex. 5 | | 0 | | 0 | | 14.2 |

*1: Other by-products were hardly produced in all Examples but 13.6 m moles and 17.8 m moles of methylal were by-produced in Comparative Examples 4 and 5.

It will be obvious from the results in Tables 3 and 7 that a dialkyl oxalate can be effectively produced according to this invention, whereas an extremely poor selectivity of a dialkyl oxalate is obtained according to the prior process (as seen in Comparative Example 2); the reaction of the prior process does in no way proceed if a dehydrating agent is not employed (as seen in Comparative Example 3); and further that a dialkyl oxalate is hardly produced if an alkali metal halide is used as a reaction accelerator (as seen in Comparative Examples 4 and 5).

What is claimed is:

1. A process for the preparation of a dialkyl oxalate by reacting an alkanol having from 1 to 6 carbon atoms with carbon monoxide and oxygen under pressure, which is characterized in that the reaction is carried out in the presence of
   a. a catalyst consisting of a mixture of from 0.01 to 1.0 g. of a salt of a platinum group metal per 100 ml. of said alkanol, and from 1 to 20 parts by weight of a salt of copper or iron per part by weight of said platinum group metal salt, and
   b. at least one accelerator selected from the group consisting of carbonates, hydrogen carbonates, nitrates, sulfates, hydroxides and carboxylates of an alkali metal and of an alkaline earth metal, pyridine, quinoline, glycine, alanine, urea, thiourea, formamide, acetamide, acetylacetone, ethyl acetoacetate, dimethylglyoxime, trimethylamine, triethylamine, a tripropylamine, a tributylamine, triphenyl phosphine and a triphenyl phosphine having a halogen, methyl, ethyl, nitro or amino substituent, the amount of accelerator (b) being from 0.01 to 5 moles per mole of catalyst (a).

2. The process as claimed in claim 1, in which at least one accelerator is selected from the group consisting of carbonates, hydrogen carbonates, nitrates, sulfates and hydroxides of an alkali metal and of an alkaline earth metal.

3. The process as claimed in claim 1, in which at least one accelerator is selected from the group consisting of carbonates, hydrogen carbonates, nitrates, sulfates and hydroxides of sodium or potassium.

4. The process as claimed in claim 1, in which at least one accelerator is selected from the group consisting of pyridine, quinoline, glycine, alanine, urea, thiourea, formamide, acetamide, acetylacetone, ethyl acetoacetate, dimethylglyoxime, trimethylamine, triethylamine, a tripropylamine, a tributylamine, triphenyl phosphine and a triphenyl phosphine having a halogen, methyl, ethyl, nitro or amino substituent, the amount of accelerator (b) being from 0.01 to 5 moles per mole of catalyst (a).

5. The process as claimed in claim 1, in which the salt of a platinum group metal is platinum chloride or palladium chloride.

6. The process as claimed in claim 1, in which the salt of copper or iron is cupric chloride or ferric chloride.

7. The process as claimed in claim 1, in which the platinum group metal salt is used in an amount of 0.05 – 0.5 g. per 100 ml. of the alkanol.

8. The process as claimed in claim 1, in which the accelerator is employed in a molar amount of 0.05 – 2.5 times the amount of the catalyst.

9. The process as claimed in claim 2, in which the accelerator is employed in a molar amount of 0.5 – 2.5 times the amount of the catalyst.

10. The process as claimed in claim 4, in which the accelerator is an organic compound and is employed in a molar amount of 0.5 – 30 times the amount of the salt of a platinum group metal.

11. The process as claimed in claim 4, in which the accelerator is an organic compound and is employed in a molar amount of 1.0 – 20 times the amount of the salt of a platinum group metal.

12. The process as claimed in claim 1, in which the reaction temperature is between 40° and 150° C.

13. The process as claimed in claim 1, in which the reaction temperature is between 60° and 120° C.

14. The process as claimed in claim 1, in which carbon monoxide pressure is between 40 and 120 Kg./cm$^2$G.

15. The process as claimed in claim 1, in which oxygen pressure is not more than 20 Kg./cm$^2$G.

* * * * *